US005495857A

United States Patent [19]

Fegan

[11] Patent Number: 5,495,857

[45] Date of Patent: Mar. 5, 1996

[54] THERAPEUTIC ENCLOSURE FOR A PATIENT

[76] Inventor: Kevin Fegan, 245 Meyersville Rd., Meyersville, N.J. 07933

[21] Appl. No.: 254,600

[22] Filed: Jun. 6, 1994

[51] Int. Cl.[6] .............................. A61F 5/37; A61G 10/00

[52] U.S. Cl. .............................................. 128/846; 600/21

[58] Field of Search .............................. 128/846, 205.26, 128/202.12; 600/21, 22

[56] References Cited

U.S. PATENT DOCUMENTS

| | | | |
|---|---|---|---|
| 1,892,378 | 12/1932 | Bernstein | 128/205.26 |
| 2,190,613 | 2/1940 | Sittler | 128/205.26 |
| 2,980,112 | 4/1961 | Snyder | 128/205.26 |
| 3,000,379 | 9/1961 | Viers | 600/21 |
| 3,602,221 | 8/1971 | Bleiken | 128/205.26 |
| 3,889,670 | 6/1975 | Loveland | 128/205.26 |
| 4,233,970 | 11/1980 | Kranz | 128/205.24 |
| 4,773,767 | 9/1988 | Coll | 374/147 |

*Primary Examiner*—Michael A. Brown
*Attorney, Agent, or Firm*—Alfred C. Hill

[57] ABSTRACT

A therapeutic enclosure for a patient having a framework arrangement having a predetermined configuration; a transparent plastic material covering at least the framework to provide the enclosure for the patient; and a temperature sensitive strip secured to a predetermined location on the plastic material to measure a temperature within the enclosure and to be observable from an exterior of the enclosure.

11 Claims, 1 Drawing Sheet

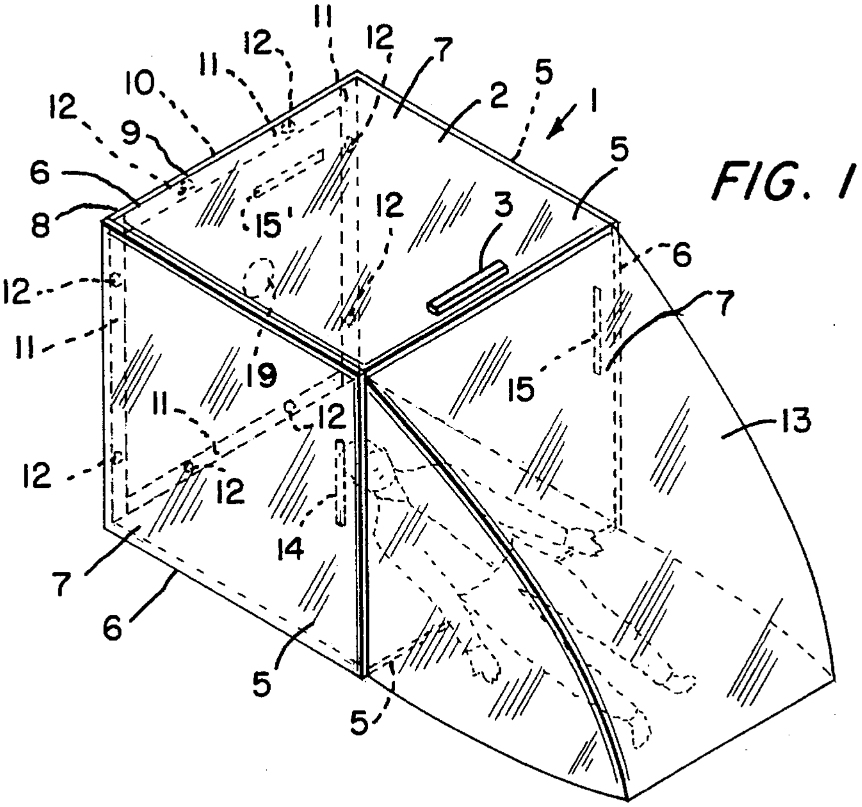
FIG. 1
FIG. 2
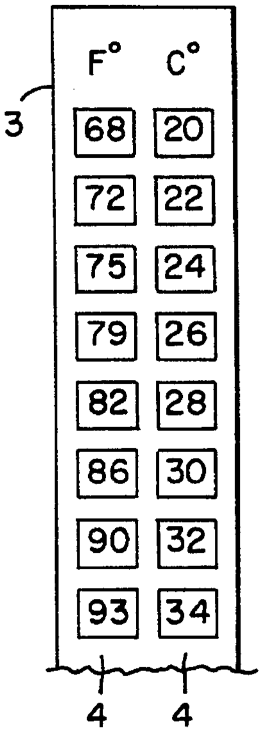
FIG. 3
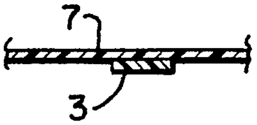
FIG. 5
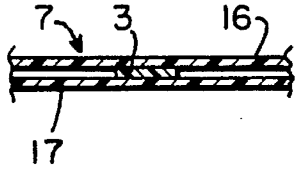
FIG. 4
FIG. 6
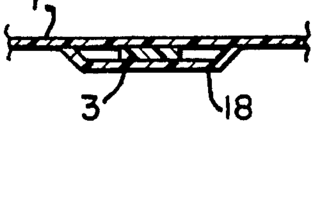

THERAPEUTIC ENCLOSURE FOR A PATIENT

BACKGROUND OF THE INVENTION

The present invention relates to means for controlling environments in medical treatment applications, and more particularly to an enclosure for maintaining an enriched oxygen and/or vapor environment in the region about a patient's head and upper body.

Nebulized vapor or mist is widely recognized as an effective therapy to alleviate the symptoms of croup, asthma and upper respiratory disease in general. Devices for providing moist air therapy are available for hospital and household settings. In hospitals, the typical approach is to employ an oxygen tent constructed of flexible, pliable and transparent plastic sheeting or film, draped over a bed to form an enclosure surrounding at least the upper body of the patient. Oxygen is supplied to the tent interior, usually at a controlled, steady rate. The oxygen supplied to the tent can be humidified and medicated to the extent desired. In such arrangements, it is particularly difficult to monitor the temperature of such a tent, so that the patient within the tent can be maintained in a comfortable condition. The usual practice to monitor the temperature within the tent is to employ a glass mercury or alcohol thermometer which is held by a medical professional in an aperture in the tent to thereby measure the temperature within the tent so that the temperature can be controlled.

There is such a tent arrangement on the market that includes a pocket to hold the breakable, glass mercury or alcohol thermometer so that medical personnel do not have to hold the breakable thermometer to measure the temperature within the tent.

The employment of breakable thermometers, such as mercury and alcohol thermometers, are dangerous for the personnel handling the thermometer as well as the patient should the thermometer break and allow the mercury or alcohol to escape to the interior of the tent.

U.S. Pat. No. 5,245,998 discloses a humidity concentrating tent which has no provisions for monitoring the temperature within the tent.

U.S. Pat. No. 4,635,630 discloses apparatus for heat therapy by inhalation which does provide arrangements for measuring the temperature within the inhalation apparatus which consists of a bimetallic strip thermometer that extends through the inhalation device from the outside to the inside thereof.

Neither of these patents disclose a temperature sensitive strip secured to a surface of the tent itself to measure the temperature within a tent or inhalation device.

SUMMARY OF THE INVENTION

An object of the present invention is to provide a therapeutic enclosure for a patient containing a built in thermometer to monitor and measure the temperature within the enclosure.

Another object of the present invention is to provide a therapeutic enclosure for a patient having a built in liquid crystal thermometer to enable measuring the temperature within the enclosure.

A feature of the present invention is the provision of a therapeutic enclosure for a patient comprising framework means having a predetermined configuration; transparent plastic means covering at least the framework means to provide the enclosure for the patient; and a temperature sensitive strip secured to a predetermined location on the plastic means to measure a temperature within the enclosure and to be observable from an exterior of the enclosure.

Another feature of the present invention is the provision of a disposable and collapsible therapeutic enclosure for a patient comprising a predetermined number of panels having frame members interconnected by and covered with a first transparent plastic means and a connecting panel having a frame member covered with a second transparent plastic means, portions of the first and second plastic means having means to connect the predetermined number of panels and the connecting panel to provide a portion of the enclosure having a predetermined configuration, the first plastic means having a portion thereof extending beyond the predetermined number of panels to provide a canopy to complete the enclosure; and a temperature sensitive strip secured to a predetermined location on the first transparent plastic means to measure a temperature within the enclosure and to be observable from an exterior of the enclosure.

BRIEF DESCRIPTION OF THE DRAWING

Above-mentioned and other features and objects of the present invention will become more apparent by reference to the following description taken in conjunction with the accompanying drawing, in which:

FIG. 1 is a perspective view of a therapeutic enclosure for a patient in accordance with the principles of the present invention;

FIG. 2 is an enlarged view of the liquid crystal thermometer employed in the enclosure of FIG. 1;

FIG. 3 is a partial cross-sectional view of FIG. 1 illustrating one embodiment of the location of the strip thermometer on the enclosure of FIG. 1 in accordance with the principles of the present invention;

FIG. 4 is a partial cross-sectional view of FIG. 1 illustrating another embodiment of the location of the strip thermometer on the enclosure of FIG. 1 in accordance with the principles of the present invention;

FIG. 5 is a partial cross-sectional view of FIG. 1 illustrating still another embodiment of the location of the strip thermometer on the enclosure of FIG. 1 in accordance with the principles of the present invention; and FIG. 6 is a partial cross-sectional view of FIG. 1 illustrating a further embodiment of the location of the strip thermometer on the enclosure of FIG. 1 in accordance with the principles of the present invention.

DESCRIPTION OF THE PREFERRED EMBODIMENTS

Referring to FIGS. 1 and 2, the therapeutic enclosure for a patient in accordance with the principles of the present invention includes a framework 1 having a predetermined configuration shown in FIG. 1 as a cube, but which could be triangular, or a three dimensional rectangular shape. A transparent plastic means 2 covers at least the framework means 1 to provide the enclosure for the patient. A temperature sensitive strip 3 is secured to a predetermined location on the plastic means 2 to measure a temperature within the enclosure and to be observable from an exterior of the enclosure by medical personnel. Temperature sensitive strip 3 as illustrated in FIG. 2 is a series of liquid crystal films 4 which changes color and illuminates at specific temperatures. The liquid crystal thermometer gives a clearly illuminated-liquid crystal display of the internal temperature of the enclosure in both Fahrenheit and Centigrade simultaneously. The strip thermometer 3 adheres to either the inside or the outside of the enclosure and accurate readings are clearly visible by medical personnel external of the enclosure even if thermometer 3 is located on the inside of the enclosure due to the transparent plastic material forming the enclosure.

Framework means 1 includes as illustrated in FIG. 1 a predetermined number of panels 5, four in number in the illustration of FIG. 1, having frame members 6 interconnected by and covered with a first transparent, continuous plastic means 7. A connecting panel 8 has a frame member 9 covered with a second transparent plastic means 10. The first plastic means 7 includes flanges 11 which carry in conjunction with the second plastic means 108 snap arrangements 12 which connect the predetermined number of panels 5 to the connecting panel 8 to provide a portion of the enclosure having the desired and predetermined configuration. The first plastic means 7 includes a portion thereof extending beyond the predetermined number of panels 5 to provide a canopy 13 to complete the enclosure and cover the patient.

As indicated in FIG. 1, the strip thermometer 3 can be disposed and secured to the top portion of the enclosure as indicated by the solid outline thereon. Alternatively, the strip thermometer 3 can be disposed on either side of the enclosure as indicated by the dotted regions 14 and 15, or on the back of the enclosure as indicated by dotted region 151.

As shown in FIG. 3, the strip thermometer 3 can be disposed on the inner surface of the plastic means 7 so that the temperature readings thereof are visible from the outside of the enclosure.

Alternatively, the strip thermometer 3 can be secured to the outer surface of the plastic means 7 as shown in FIG. 4.

The first transparent plastic means 7 can be provided by two layers of plastic material 16 and 17 to interconnect the predetermined number of panels and to enclose the frame members of these panels. In this arrangement as shown in FIG. 5, the strip thermometer 3 is disposed between the layers 16 and 17 to protect the strip thermometer 3.

FIG. 6 shows an alternative arrangement to that of FIG. 5 to protect the strip thermometer 3. In this case, the strip thermometer 3 is protected by a plastic sheet 18 covering the strip thermometer 3 and encapsulating the same to better secure it to the enclosure.

Aperture 19 shown in FIG. 1 is provided in connecting panel 8 to enable supplying oxygen and/or vapor and/or medicine to the interior of the enclosure.

When the therapeutic enclosure of the present invention as described hereinabove is employed, a built in strip thermometer is provided along with the therapeutic enclosure so that there is no guesswork as to the temperature within the enclosure and there is no possibility of breaking a breakable glass thermometer whether it be a mercury-type or an alcohol-type thermometer.

While I have described above the principles of my invention in connection with specific apparatus it is to be clearly understood that this description is made only by way of example and not as a limitation to the scope of my invention as set forth in the objects thereof and in the accompanying claims.

I claim:

1. A therapeutic enclosure for a patient comprising:

framework means having a predetermined configuration;

transparent plastic means cove:ring at least said framework means to provide said enclosure for said patient; and a temperature sensitive strip secured to an outside of said plastic means to measure a temperature within said enclosure and to be observable from an exterior of said enclosure.

2. An enclosure according to claim 1, wherein said temperature sensitive strip is a liquid crystal strip thermometer.

3. A therapeutic enclosure for a patient comprising:

framework means having a predetermined configuration;

transparent plastic means covering at least said framework means to provide said enclosure for said patient; and a temperature sensitive strip secured to a predetermined location on said plastic means to measure a temperature within said enclosure and to be observable from an exterior of said enclosure;

said plastic means including two layers of plastic material enclosing at least certain parts of said framework means, and said temperature sensitive strip is secured between said two layers of plastic material to protect said temperature sensitive strip.

4. A therapeutic enclosure for a patient comprising:

framework means having a predetermined configuration;

transparent plastic means covering at least said framework means to provide said enclosure for said patient; and a temperature sensitive strip secured to a predetermined location on said plastic means to measure a temperature within said enclosure and to be observable from an exterior of said enclosure;

said temperature sensitive strip being a liquid crystal strip thermometer;

said plastic means including two layers of plastic material enclosing at least certain parts of said framework means, and said strip thermometer is secured between said two layers of plastic material to protect said strip thermometer.

5. A disposable and collapsible therapeutic enclosure for a patient comprising:

a predetermined number of panels having frame members interconnected by and covered with a first transparent plastic means and a connecting panel having a frame member covered with a second transparent plastic means, portions of said first and second plastic means having means to connect said predetermined number of panels and said connecting panel to provide a portion of said enclosure having a predetermined configuration, said first plastic means having a portion thereof extending beyond said predetermined number of panels to provide a canopy to complete said enclosure; and a temperature sensitive strip secured to a predetermined location on said first transparent plastic means to measure a temperature within said enclosure and to be observable from an exterior of said enclosure.

6. An enclosure according to claim 5, wherein said temperature sensitive strip is liquid crystal strip thermometer.

7. An enclosure according to claim 6, wherein said strip thermometer is secured to an inside of said plastic means.

8. An enclosure according to claim 7, further including a plastic sheet covering said strip thermometer to protect said strip thermometer.

9. An enclosure according to claim 8, wherein said plastic sheet is a MYLAR sheet.

10. An enclosure according to claim 6, wherein said strip thermometer is secured to an outside of said plastic means.

11. An enclosure according to claim 6, wherein said first transparent plastic means includes two layers of plastic material enclosing at least certain ones of said frame members of said predetermined number of panels, and said strip thermometer is secured between said two layers of plastic material to protect said strip thermometer.

* * * * *